US006985083B2

(12) United States Patent
Yost et al.

(10) Patent No.: US 6,985,083 B2
(45) Date of Patent: Jan. 10, 2006

(54) MARKING ELECTRICAL WIRING WITH CONDITION INDICATORS

(75) Inventors: William T. Yost, Newport News, VA (US); Daniel F. Perey, Yorktown, VA (US); K. Elliott Cramer, Newport News, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 153 days.

(21) Appl. No.: 10/419,424

(22) Filed: Apr. 21, 2003

(65) Prior Publication Data

US 2003/0201901 A1 Oct. 30, 2003

Related U.S. Application Data

(60) Provisional application No. 60/453,337, filed on Mar. 4, 2003, and provisional application No. 60/376,364, filed on Apr. 24, 2002.

(51) Int. Cl.
*G08B 17/10* (2006.01)

(52) U.S. Cl. ............ 340/632; 340/605; 174/25 R
(58) Field of Classification Search ............. 340/632, 340/605, 539.27; 416/61, 241 R; 174/25 R, 174/25 C, 31.03, 110 R, 118, 120
See application file for complete search history.

(56) References Cited

U.S. PATENT DOCUMENTS

| | | | |
|---|---|---|---|
| 3,493,484 A | 2/1970 | Berg et al. | 340/7 R |
| 3,812,362 A | 5/1974 | Larsen et al. | 250/370 |
| RE28,915 E | 7/1976 | Ogden et al. | 340/237 S |
| 4,088,986 A | 5/1978 | Boucher | 340/237 |
| 4,148,022 A | 4/1979 | Hetznecker | 340/628 |
| 4,223,559 A | 9/1980 | Chuan et al. | 73/432 |
| 4,745,399 A | 5/1988 | Kimura | 340/521 |
| 4,882,576 A | 11/1989 | Boyd | 340/632 |
| 5,065,140 A | 11/1991 | Neuburger | 340/634 |
| 5,079,542 A | 1/1992 | Umezawa | 340/587 |
| 5,250,908 A | 10/1993 | Liu et al. | 324/542 |
| 5,376,888 A | 12/1994 | Hook | 324/643 |
| 5,424,895 A | 6/1995 | Gaston | 361/46 |
| 5,541,803 A * | 7/1996 | Pope et al. | 361/103 |
| 5,793,296 A | 8/1998 | Lewkowicz | 340/632 |
| 5,862,030 A * | 1/1999 | Watkins et al. | 361/103 |
| 6,085,576 A | 7/2000 | Sunshine et al. | 73/29.01 |
| 6,111,512 A | 8/2000 | Sugimoto et al. | 340/577 |
| 6,456,471 B1 | 9/2002 | Haun et al. | 361/42 |
| 6,477,021 B1 | 11/2002 | Haun et al. | 361/42 |
| 6,512,444 B1 * | 1/2003 | Morris et al. | 337/401 |
| 2002/0089335 A1 | 7/2002 | Williams | 324/533 |
| 2002/0109166 A1 | 8/2002 | Hsu et al. | 257/295 |
| 2002/0121983 A1 | 9/2002 | Boyden | 340/635 |
| 2002/0125891 A1 | 9/2002 | Allan et al. | 324/534 |

FOREIGN PATENT DOCUMENTS

| | | |
|---|---|---|
| EP | 0681179 A1 | 11/1995 |
| WO | WO 9215973 A1 | 9/1992 |

OTHER PUBLICATIONS

Reliable Fire Equipment Company, HCL Early Detection Systems, 1998, http://www.reliablefire.com/HCLfolder/hcl-detsystems.html.*

* cited by examiner

*Primary Examiner*—Jeffery Hofsass
*Assistant Examiner*—Jennifer Stone
(74) *Attorney, Agent, or Firm*—Kurt G. Hammerle

(57) ABSTRACT

A method is provided for marking electrical wiring with condition indicators. One or more markers are added to one or both of the insulative material and a surface of an electrical conductor such that it bonds thereto. Each marker is capable of emanating into a surrounding atmospheric environment as a gaseous effluent in response to a specific condition experienced by the electrical conductor.

18 Claims, 5 Drawing Sheets

MARKING ELECTRICAL WIRING WITH CONDITION INDICATORS

CLAIM OF BENEFIT OF PROVISIONAL APPLICATION

Pursuant to 35 U.S.C. § 119, the benefit of priority from provisional application U.S. Ser. No. 60/453,337, with a filing date of Mar. 4, 2003, and from provisional application U.S. Ser. No. 60/376,364, with a filing date of Apr. 24, 2002, is claimed for this non-provisional application.

ORIGIN OF THE INVENTION

The invention described herein was made by employees of the United States Government and may be manufactured and used by or for the Government for governmental purposes without the payment of any royalties thereon or therefor.

CROSS-REFERENCE TO RELATED APPLICATION

This patent application is co-pending with one related patent application Ser. No. 10/421,409 entitled "Method for Anticipating Problems with Electrical Wiring," filed Apr. 21, 2003, and owned by the same assignee as this patent application (NASA Case No. LAR 16327-1).

BACKGROUND OF THE INVENTION

1. Field of the Invention

This invention relates to assessment of an electrical wire. More specifically, the invention is a method for adding markers that can emanate from electrical wiring as a gaseous effluent, where each gaseous effluent is monitored to indicate a specific condition experienced by the wiring, such condition potentially affecting the future integrity of the electrical wiring.

2. Description of the Related Art

Wiring (e.g., individual conductors, bundles of conductors, conductive runs on printed circuit boards, etc.) is used extensively for the delivery of electrical power and electrically coded information. Although wiring is typically presumed to be stable and avoid degradation, the reality is that many applications are critically affected by aging of electrical insulation disposed about an electrical conductor. For example, insulation may be adversely affected by moisture and heat. As the insulation ages, the loss-tangent of the material changes thereby changing the frequency response and power loss of the associated electrical conductors. In power transmission applications, electrical insulation plays a key role in the prevention of shorts and arcs. Specifically, insulation degradation can cause functional failures such as frequency attenuation and short circuits. Such failures may lead to problems ranging from annoying brief interruptions of service to lengthy catastrophic system failures.

SUMMARY OF THE INVENTION

The invention is a method for marking electrical wiring with condition indicators and a method for anticipating problems with electrical wiring. The electrical wiring comprises at least one electrical conductor having an insulative material, the insulative material being in contact with the electrical conductor and providing electrical insulation properties. At least one marker is added to one or both of the insulative material and a surface of the electrical conductor such that it bonds thereto. Each marker is capable of emanating into a surrounding atmospheric environment as a gaseous effluent in response to a specific condition experienced by the electrical conductor during its useful life. Electrical wiring marked in this fashion can be monitored in order to anticipate future problems. Specifically, the atmospheric environment around the electrical wiring is monitored for the gaseous effluent. An alarm signal can be generated when a predetermined level of the gaseous effluent is detected.

DETAILED DESCRIPTION OF THE INVENTION

Figure 1:
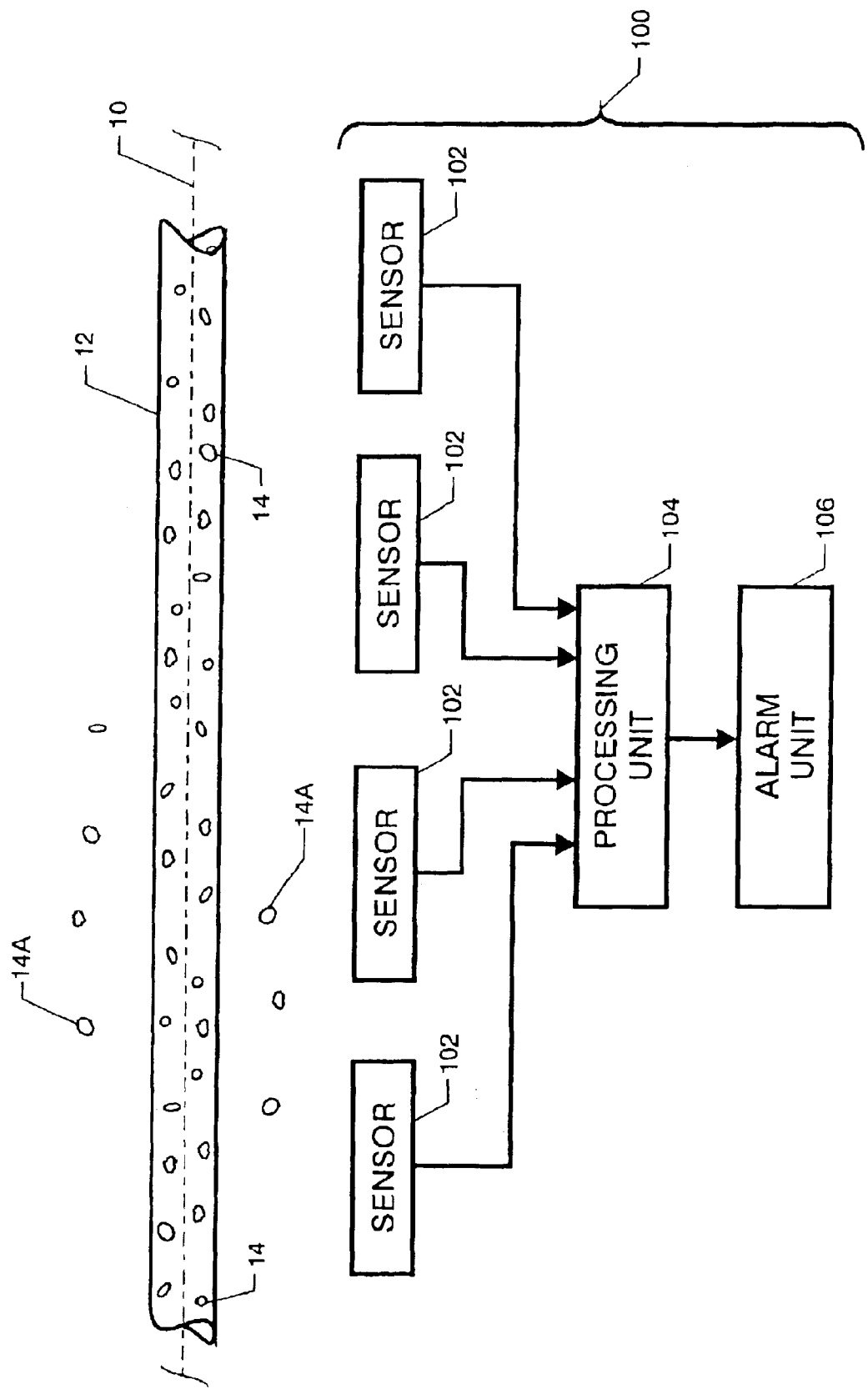
FIG. 1 is a schematic view of a system for passively assessing the insulative material of electrical wiring in accordance with the present invention.

Referring now to the drawings, and more particularly to FIG. 1, one embodiment of a system for assessing electrical wiring in accordance with the present invention is shown and referenced generally by numeral 100. More specifically, system 100 anticipates problems with the insulative material of electrical wiring. Such wiring is represented in FIG. 1 by an electrical conductor 10 that has an electrically insulative material 12 in contact therewith. For each embodiment described herein, it is to be understood that the conductor 10 is representative of both a standard electrically conductive wire and an electrically conductive run (on a printed circuit board (PCB)) where the insulation and the PCB material, respectively, serve as insulative material 12.

Insulative material 12 is any material that possesses electrical insulation properties, a variety of which are well known in the art. During normal processing of insulative material 12, one or more impurities 14 molecularly bond to material 12 without affecting the electrical or structural integrity of material 12. Such bonding can occur within or throughout the insulative material 12 or on the surface of insulative material 12. For example, if material 12 were dyed during the processing thereof, impurities 14 would be in the form of the dye(s) that impregnated insulative material 12. In another example, if insulative material 12 were printed upon during the processing thereof, the printing ink would form impurities 14 on the surface of insulative material 12. In either case, the present invention takes advantage of the fact that the molecular bonding or attachment energy coupling impurities 14 to insulative material 12 is generally relatively weak.

During the normal useful life of conductor 10, electric current will pass therethrough thereby causing a certain low level of heat to be generated in conductor 12. Over time, the low levels of heat tend to cause the conductor's insulative material to degrade. Additionally, greater levels of heat are generated in conductor 10 if there has been damage thereto.

Such damage could be caused by various forms of mechanical stresses (e.g., bending, cuts, chafing, etc.), environmental stresses (e.g., high temperatures, excessive moisture, etc.), or operational stresses (e.g., current surges, over-voltage conditions, etc.). It has been discovered that both high and low levels of heat energy can break the relatively weak molecular bond that couples impurities 14 to insulative material 12. When these bonds break, impurities 14 escape or emanate from insulative material 12 in a gaseous effluent form, designated in FIG. 1 by reference numeral 14A.

At normal operating loads where the heat experienced by conductor 10 is relatively low, gaseous effluent 14A tends to emanate from insulative material 12 slowly and at a fairly steady rate. However, if conductor 10 has undergone some form of mechanical, environmental, or operational stress, or any combination thereof, that causes a greater amount of heat to be generated in the conductor, the rate of escape of gaseous effluent 14A can be substantially greater than the rate experienced at normal operating currents. By monitoring the presence and/or levels of gaseous effluent 14A, the present invention provides a method and system for anticipating problems with conductor 10.

For example, the system could continually monitor for gaseous effluent 14A and generate an alarm when one of the following events occurs:

(i) the levels of gaseous effluent 14A increase to some predetermined level that indicates the occurrence of a stressful event; or (ii) the levels of gaseous effluent 14A decrease to some predetermined level that indicates the possible onset of degradation of the insulative material because a reduced level of gaseous effluent 14A normally occurs when the level of impurities in the insulative material 14 becomes substantially or completely depleted. Such reduced or non-existent levels of gaseous effluent 14A could signify that a number of stressful events had already occurred. Thus, another approach of the present invention would involve monitoring the presence of gaseous effluent 14A, where the presence of gaseous effluent 14A is indicative of viable insulative material 12 while the absence of gaseous effluent 14A is indicative of degraded insulative material 12.

To achieve the above-described methodology, system 100 includes one or more sensors 102 positioned along and in the vicinity of conductor 10. Each of sensors 102 is capable of monitoring a local environment for gaseous effluent 14A. Sensor outputs are supplied to a processing unit 104 that is programmed with one or more predetermined levels for comparison with the levels of gaseous effluent 14A monitored by sensors 102. As mentioned above, a low predetermined level (meaning levels of impurities 14 are greatly diminished) could be used to signify the normal aging of conductors 10 while a high predetermined level could be used to signify the occurrence of a stressful event. In either case, once gaseous effluent 14A attains one of the predetermined levels, processing unit 104 sends an alarm signal to an alarm unit 106 which can be realized by one or more audio and/or visual alarm devices. The particular sensor 102 that detects a high or low level of gaseous effluent 14A also provides a general location of the anticipated wiring problem so that the conductor 10 can be repaired or replaced.

Monitoring of gaseous effluent 14A by sensors 102 in each of the embodiments described herein can be accomplished in a variety of ways. Accordingly, it is to be understood that each of sensors 102 is representative of a variety of well known systems or techniques used to monitor levels of gaseous substances such as gaseous effluent 14A. Such systems and techniques include, but are not limited to, optical systems and techniques that detect a unique absorption at specific wavelengths of the electromagnetic spectrum; gas chromatography systems and techniques that segregate effluents by size and/or mass and determine the amount of segregated effluents; colorimetry systems and techniques; electromagnetic detection systems and techniques, such as optical fiber systems or other spectrophotometric techniques; and ultrasonic systems and techniques that monitor changes in scattering, absorption, wave propagation speed change, and non-linear effects that depend on changes in the ratio of gaseous specific heats.

Figure 2:
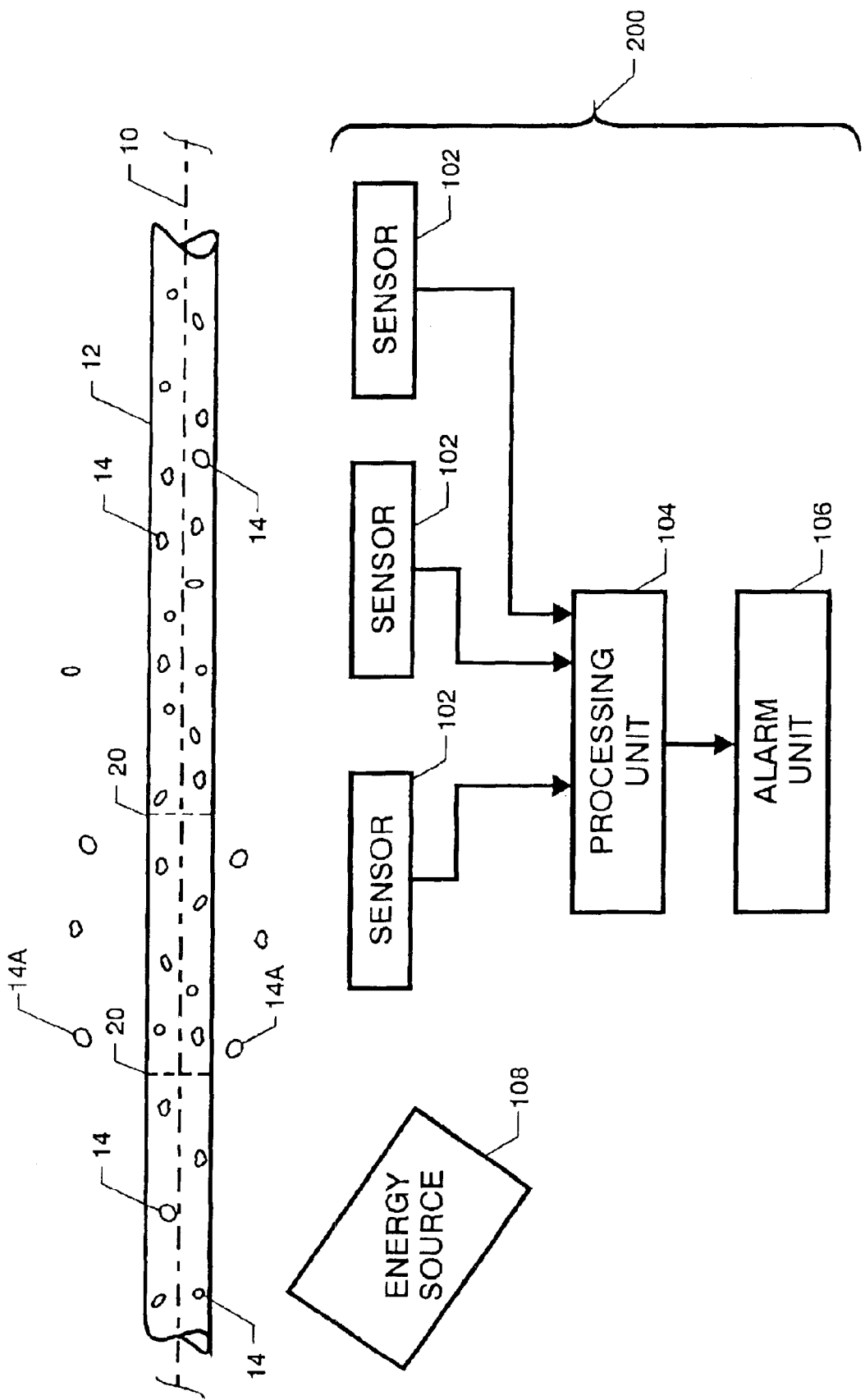
FIG. 2 is a schematic view of a system for actively assessing the insulative material of electrical wiring in accordance with the present invention.

The present method and system can also be used in a "spot check" fashion as illustrated by the embodiment depicted in FIG. 2 where like reference numerals are used for those elements in common with the embodiment of FIG. 1. More specifically, a system 200 comprises an energy source 108 capable of directing energy (e.g., heat energy) toward an area of interest (between dashed lines 20) of conductor 10 and its surrounding insulative material 12. The energy generated and directed by energy source 108 should be sufficient to cause the emanation of impurities 14 as gaseous effluent 14A. System 200 can be used in a variety of ways depending on the bonding or attachment energy associated with impurities 14. For example, if the bonding energy associated with impurities 14 is very weak, system 200 can be used to confirm whether or not any of impurities 14 remain in or on insulative material 12 in area 20. That is, if a low (or no) level of gaseous effluent 14A is detected, this condition may indicate that insulative material 12 may not have much useful life left. If, however, the bonding energy associated with impurities 14 is stronger such that only stressful situations cause emanation from insulative material 12 as gaseous effluent 14A, system 200 can be used to determine whether area 20 has experienced such stressful situations. That is, if energy source 108 can cause emanation of gaseous effluent 14A, it may be presumed that area 20 has already experienced stress and should be repaired. The monitoring aspect of system 200 operates in the same fashion under each of the above situations. Specifically, energy source 108 directs its energy toward area 20 and sensor 102, processing unit 104, and alarm unit 106 function as described earlier for the embodiment of FIG. 1.

Figure 3:
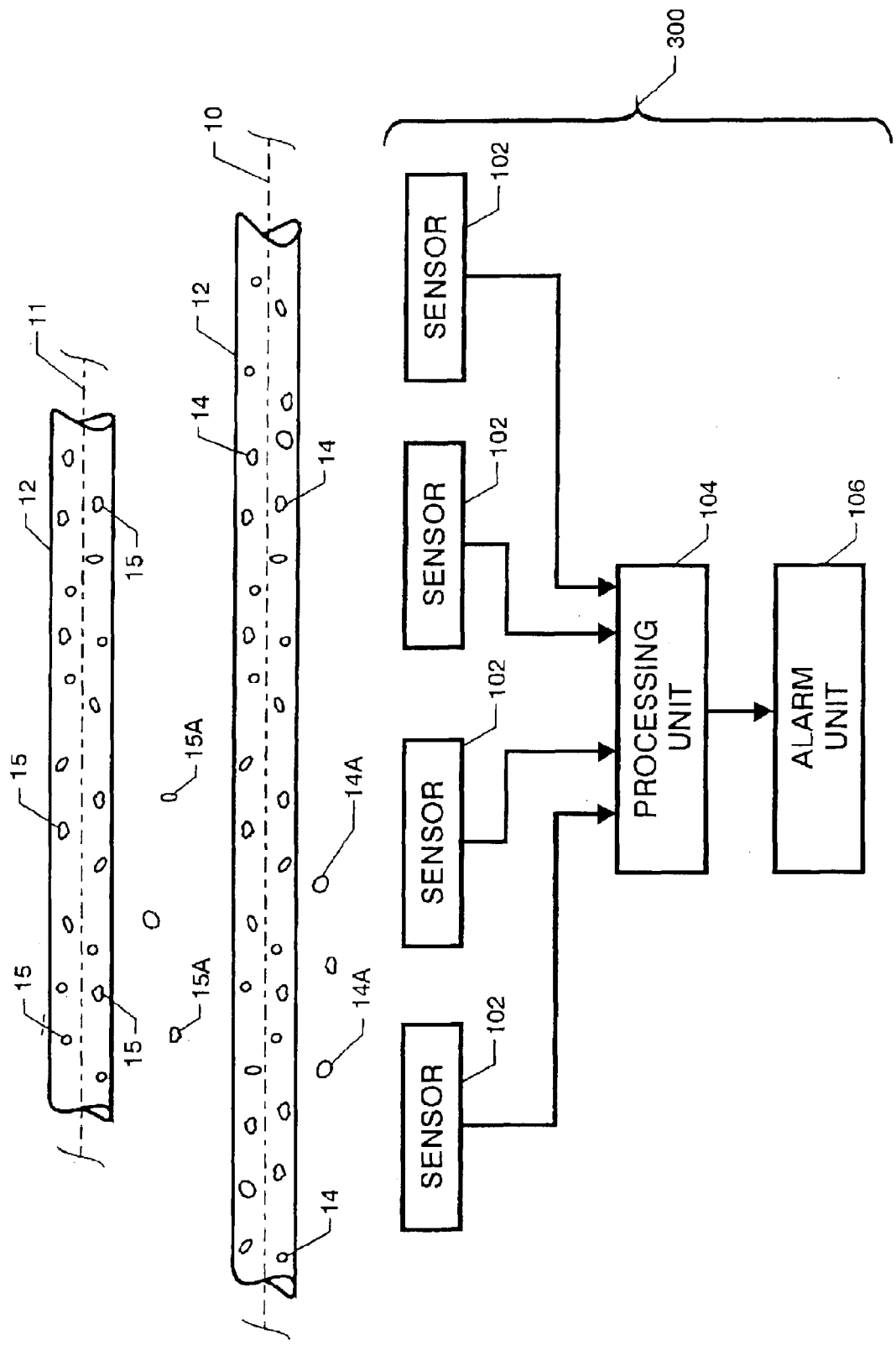
FIG. 3 is a schematic view of a system for passively assessing the insulative material of a plurality of electrical conductors in accordance with the present invention.

The present invention is not limited to use with a single conductor and can be extended for use with a plurality of conductors. By way of illustrative example, two conductors 10 and 11 are shown in FIG. 3, although more than two conductors can also be monitored. As in the previous embodiments, each of conductors 10 and 11 has insulative material 12 in contact therewith. However, impurity 14 is associated with conductor 10 while a different impurity 15 is associated with conductor 11. Accordingly, each gaseous effluent 14A and 15A is a unique substance and each of sensors 102 in system 300 is sensitive to and can distinguish between each gaseous effluent 14A and 15A. Note that each of sensors 102 is representative of a single gas discriminating sensing system or multiple dedicated sensing systems. The processing unit 104 and alarm unit 106 of system 300 function as previously described in the embodiment of FIG. 1 for each of gaseous effluent 14A and 15A.

Figure 4:
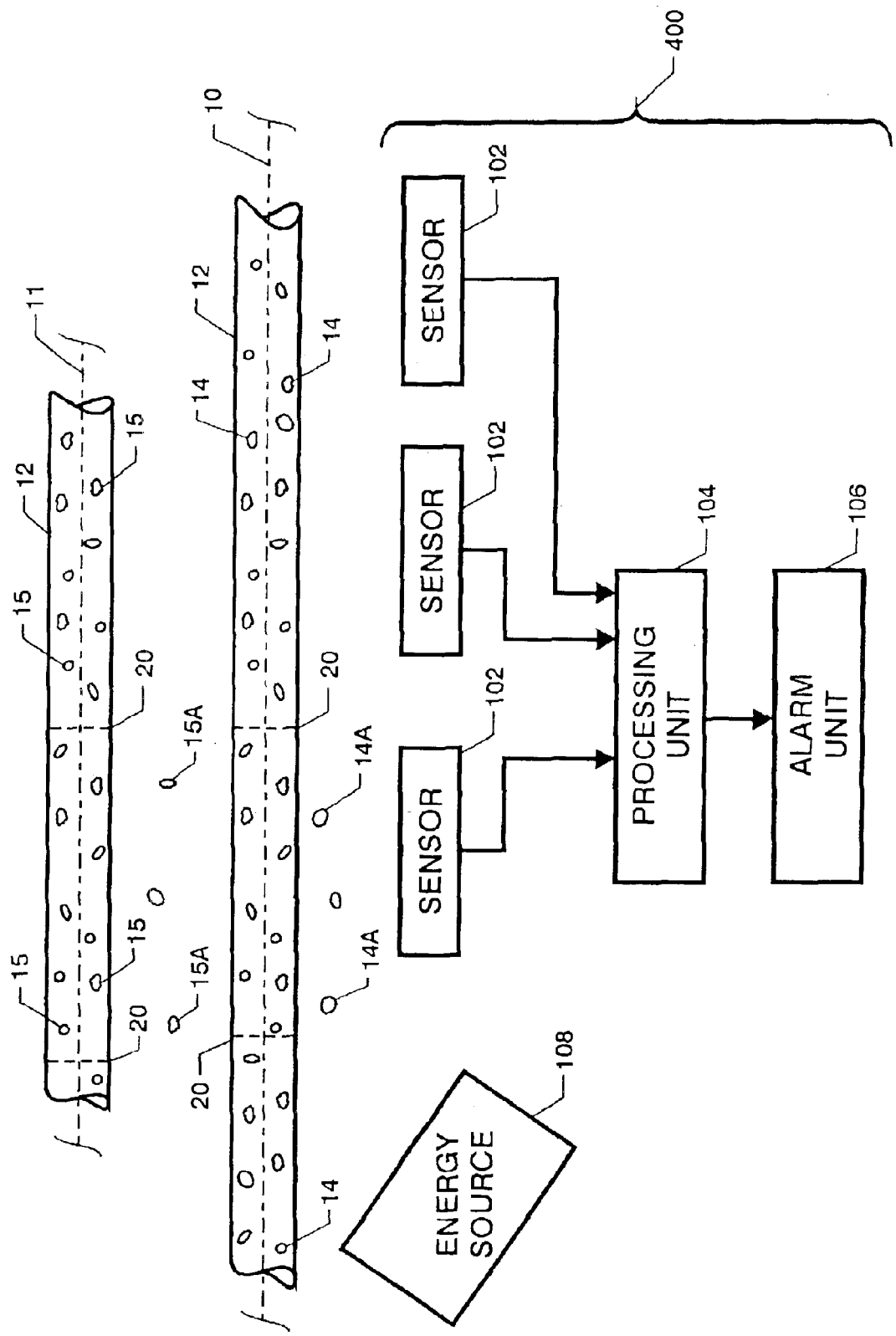
FIG. 4 is a schematic view of a system for actively assessing the insulative material of a plurality of electrical conductors in accordance with the present invention.

The present method and system can also be used to "spot check" one or more conductors in a multiple conductor situation as illustrated by system 400 of FIG. 4. Once again, like reference numerals are used for those elements in common with the previous embodiments. Similar to the system 200, system 400 includes an energy source 108 used to cause a specific one or all of gaseous effluents 14A and 15A to emanate from insulative material 12 in area 20. Sensors 102, processing unit 104 and alarm unit 106 function as previously described for the embodiments of FIGS. 1 and 2 to provide condition indications of one or all of conductors 10 and 11.

Figure 5:
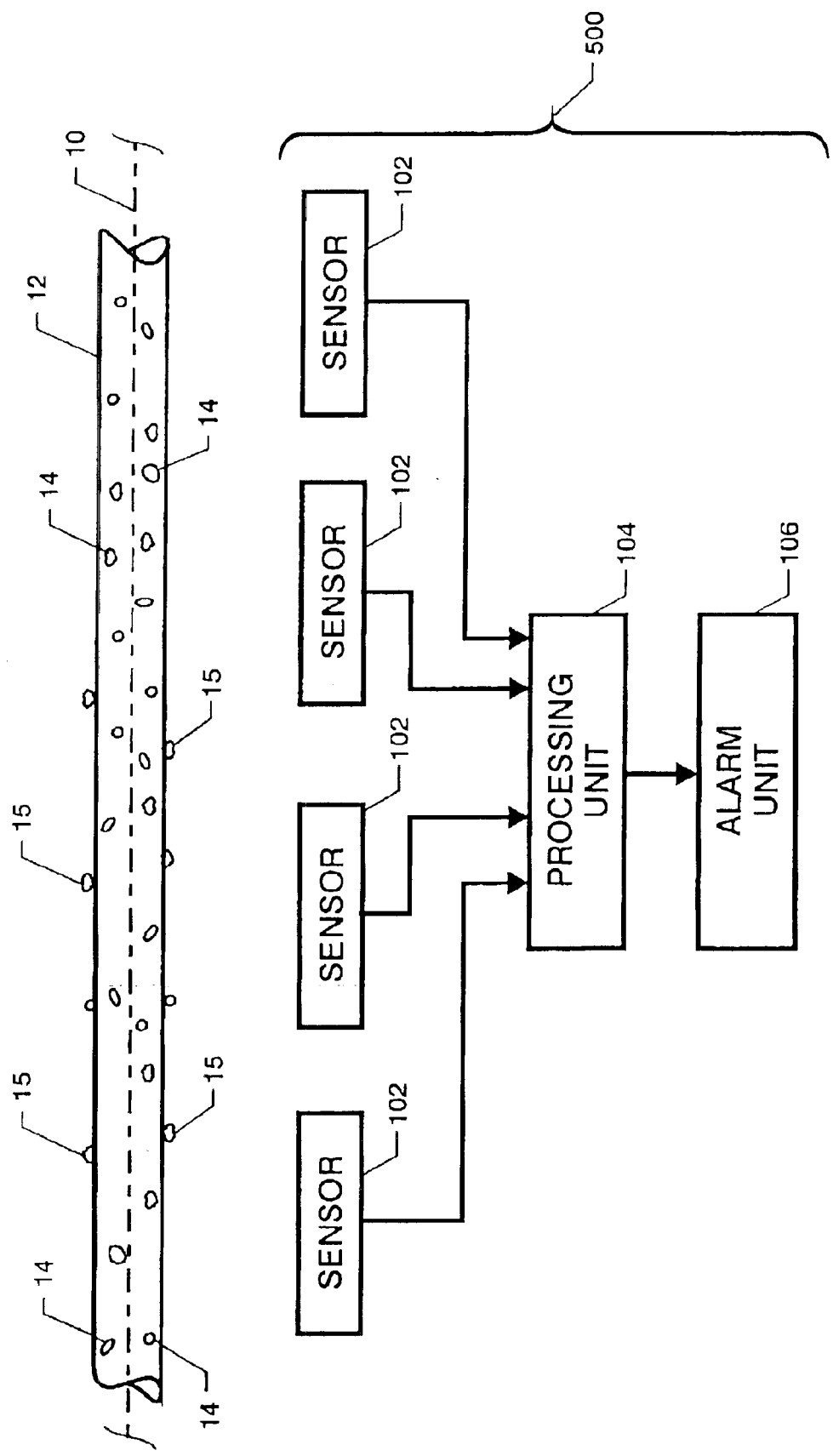
FIG. 5 is a schematic view of another embodiment of a system for passively assessing the insulative material of electrical wiring in accordance with the present invention.

The present invention has thus far been described for a single impurity associated with each conductor. However, the present invention could also be used where more than one type of impurity is associated with a conductor. For example, as illustrated in FIG. 5 for single conductor 10, insulative material 12 could have both impurities 14 and 15 impregnated therein or disposed thereon. For example, impurity 14 could be impregnated (e.g., a dye) while impurity 15 could be disposed on the surface (e.g., printed) of insulative material 12. If surface impurity 15 is released as a gaseous effluent during normal operating conditions while impregnated impurity 14 were released only during stressful operating conditions, system 500 could anticipate both normal degradation and damage caused by stressful conditions.

Each of the above-described embodiments could be intentionally designed to make specific situations of interest quickly recognizable. That is, rather than being limited by the impurities inherent in currently manufactured insulative materials, specific markers could be added to either the insulative material or directly on an electrical conductor. For example, the insulative material (e.g., wire coatings, PCBs on which conductive runs are deposited, etc.) could be intentionally and specifically marked with one or more "markers" that do not affect electrical and/or structural integrity of the insulative material. Each such marker would be selected such that it would emanate into a surrounding atmospheric environment as a gaseous effluent and in a known fashion when specific conditions of interest are experienced. Different markers could be used to indicate each of mechanical stresses, specific types of environmental or operational stresses, and normal use degradation. The markers could be disposed in or layered on the surface of the insulative material or even directly on the electrical conductor. Additionally or alternatively, the markers could be impregnated in the insulative material.

The passive and active systems and methods presented herein provide the means to anticipate electrical wiring problems before they occur. In this way, wiring repairs can be affected before overall system failure. The present invention further provides for the marking of electrical wiring with specific condition indicators. As a result, the present invention provides not only for the anticipation of electrical wiring problems, but also for the diagnosis of these problems so that both symptoms and their root causes can be analyzed and addressed.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function and step-plus-function clauses are intended to cover the structures or acts described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed as new and desired to be secured by Letters Patent of the United States is:

1. A method of marking electrical wiring with condition indicators, comprising steps for:
    providing an electrical conductor having an insulative material in contact therewith that provides electrical insulation properties; and
    adding at least one marker to at least one of said insulative material and a surface of said electrical conductor, each said marker being molecularly bonded to said at least one of said insulative material and said surface of said electrical conductor, each said marker emanating into a surrounding atmospheric environment as a gaseous effluent in response to a specific condition experienced by said electrical conductor.

2. A method according to claim 1 wherein said step for adding comprises the act of impregnating said insulative material with said at least one marker.

3. A method according to claim 1 wherein said step for adding comprises the act of depositing said at least one marker on a surface of said insulative material.

4. A method according to claim 1 wherein said step for adding comprises the act of depositing said at least one marker on said surface of said electrical conductor.

5. A method of marking electrical wiring with condition indicators, comprising steps for:
    providing an electrical conductor having an insulative material in contact therewith that provides electrical insulation properties; and
    adding a plurality of markers to at least one of said insulative material and a surface of said electrical conductor, each of said plurality of markers being molecularly bonded to said at least one of said insulative material and a surface of said electrical conductor, each of said plurality of markers emanating as a unique gaseous effluent into a surrounding atmospheric environment in response to one of a plurality of specific conditions experienced by said electrical conductor.

6. A method according to claim 5 wherein said step for adding comprises the act of impregnating said insulative material with said plurality of markers.

7. A method according to claim 5 wherein said step for adding comprises the act of depositing said plurality of markers on a surface of said insulative material.

8. A method according to claim 5 wherein said step for adding comprises the act of depositing said plurality of markers on said surface of said electrical conductor.

9. A method for anticipating problems with electrical wiring, comprising steps for:
    providing an electrical conductor having an insulative material in contact therewith that provides electrical insulation properties;
    adding at least one marker to at least one of said insulative material and a surface of said electrical conductor, each said marker emanating into a surrounding atmospheric environment as a gaseous effluent in response to a specific condition experienced by said electrical conductor;
    monitoring said atmospheric environment for said gaseous effluent; and
    generating an alarm signal when a predetermined level of said gaseous effluent is detected.

10. A method according to claim 9 wherein said step for monitoring uses at least one technique selected from the group consisting of optical techniques, gas chromatography techniques, colorimetry techniques, electromagnetic detection techniques, and ultrasonic techniques.

11. A method according to claim 9 wherein said step for adding comprises the act of impregnating said insulative material with said at least one marker.

12. A method according to claim 9 wherein said step for adding comprises the act of depositing said at least one marker on a surface of said insulative material.

13. A method according to claim 9 wherein said step for adding comprises the act of depositing said at least one marker on said surface of said electrical conductor.

14. A method for anticipating problems with electrical wiring, comprising steps for:
provinding a plurality of electrical conductors, each of said plurality of electrical conductors having an insulative material in contact therewith that provides electrical insulation properties;
adding at least one unique marker to at least one of (i) said insulative material for each of said plurality of electrical conductors and (ii) a surface of each of said plurality of electrical conductors, each said unique marker emanating into a surrounding atmospheric environment as a gaseous effluent in response to a specific condition experienced by said electrical conductor;
monitoring said atmospheric environment for said gaseous effluent of each said unique marker; and
generating an alarm signal when a predetermined level of said gaseous effluent of any said unique marker is detected.

15. A method according to claim 14 wherein said step for monitoring uses at least one technique selected from the group consisting of optical techniques, gas chromatography techniques, colorimetry techniques, electromagnetic detection techniques, end ultrasonic techniques.

16. A method according to claim 14 wherein said step for adding comprises the act of impregnating said insulative material in contact with each of said plurality of electrical conductors with said at least one unique marker.

17. A method according to claim 14 wherein said step for adding comprises the act of depositing said at least one unique marker on a surface of said insulative material in contact with each of said plurality of electrical conductors.

18. A method according to claim 14 wherein said step for adding comprises the act of depositing said at least one unique marker on said surface of each of said plurality of electrical conductors.

* * * * *